US010292826B2

(12) United States Patent
Wyss et al.

(10) Patent No.: US 10,292,826 B2
(45) Date of Patent: May 21, 2019

(54) KNEE PROSTHESIS

(71) Applicant: Orthopaedic Innovation Centre Inc., Winnipeg (CA)

(72) Inventors: Urs Wyss, Winnipeg (CA); Shahram Amiri, Vancouver (CA); Theodore Derek Vernon Cooke, Kingston (CA)

(73) Assignee: Orthopedic Innovation Centre Inc., Winnipeg, Manitoba (CA)

( * ) Notice: Subject to any disclaimer, the term of this patent is extended or adjusted under 35 U.S.C. 154(b) by 0 days.

(21) Appl. No.: 14/844,992

(22) Filed: Sep. 3, 2015

(65) Prior Publication Data

US 2016/0151162 A1  Jun. 2, 2016

Related U.S. Application Data

(63) Continuation of application No. 13/389,950, filed on Mar. 20, 2012.

(51) Int. Cl.
*A61F 2/38* (2006.01)
*A61F 2/30* (2006.01)

(52) U.S. Cl.
CPC .............. *A61F 2/3836* (2013.01); *A61F 2/38* (2013.01); *A61F 2/389* (2013.01); *A61F 2/3859* (2013.01); *A61F 2002/30327* (2013.01); *A61F 2230/0093* (2013.01); *A61F 2230/0095* (2013.01); *A61F 2250/0039* (2013.01)

(58) Field of Classification Search
CPC .. A61F 2/38; A61F 2220/0025; A61F 2/3836; A61F 2/3859; A61F 2/389

USPC ............... 623/20.21, 20.31, 20.32, 20.15
See application file for complete search history.

(56) References Cited

U.S. PATENT DOCUMENTS

| | | | | |
|---|---|---|---|---|
| 5,219,362 A | * | 6/1993 | Tuke | A61F 2/38 623/20.31 |
| 6,013,103 A | * | 1/2000 | Kaufman | A61F 2/38 623/20.15 |
| 2004/0186582 A1 | * | 9/2004 | Yasuda | A61F 2/38 623/20.21 |
| 2005/0096747 A1 | * | 5/2005 | Tuttle | A61F 2/389 623/20.32 |

* cited by examiner

*Primary Examiner* — Brian Dukert
(74) *Attorney, Agent, or Firm* — Gowling WLG (Canada) LLP

(57) ABSTRACT

A knee prosthesis comprising a femur component defining a ball-like femoral condyle and a tibia component defining a cavity on its medial side corresponding to the ball-like condyle. The knee prosthesis enables pivoting of the tibia component about the medial side of the femur component as a function of the flexion angle γ as long as there is joint compression applied to the knee prosthesis as exemplified by muscle forces, weight, and ligament tensions, to enforce contact between the tibia component and the femur component. The geometries of the spherical load bearing surfaces of the medial tibia condyle and medial femur condyle provide the kinematic degrees of freedom and the geometric constraints required for proper guiding of the rolling and sliding surfaces of the femoral component and tibial component during articulation of the present knee prosthesis.

10 Claims, 14 Drawing Sheets

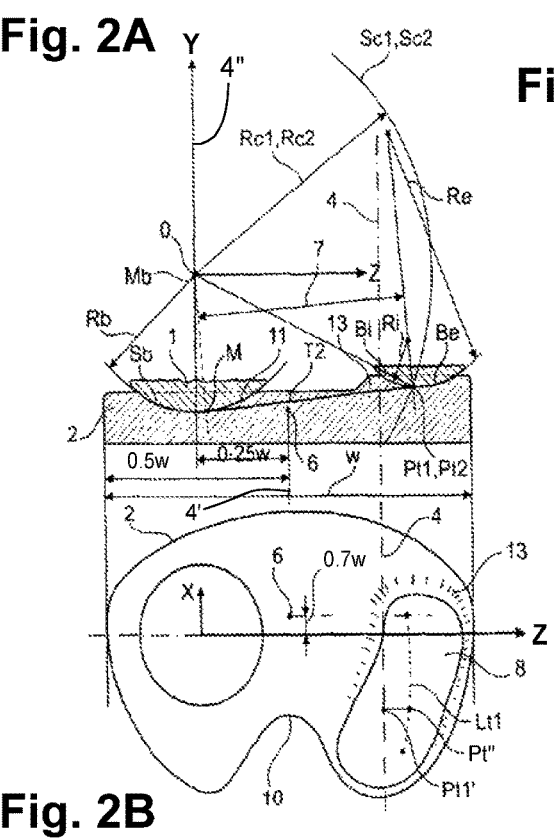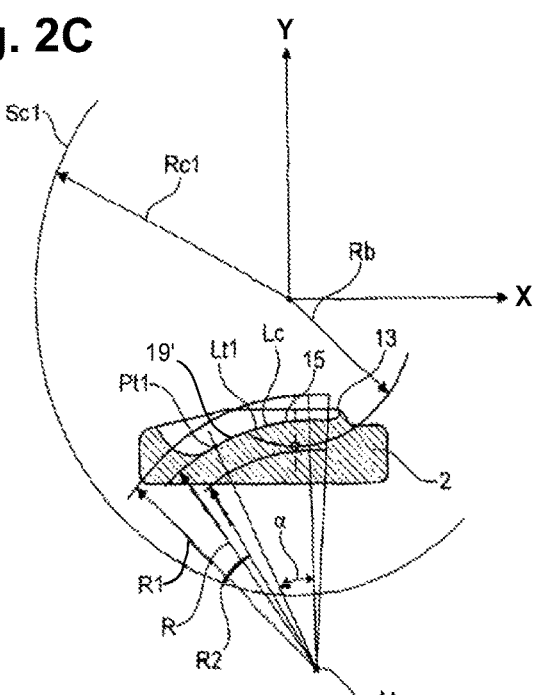

| γ[°] | Re | Ri |
|---|---|---|
| -5 | 0.66w | 0.13w |
| 0 | 0.64w | 0.15w |
| 30 | 0.55w | 0.24w |
| 60 | 0.45w | 0.34w |
| 90 | 0.35w | 0.43w |
| 120 | 0.26w | 0.53w |
| 135 | 0.21w | 0.58w |
| 150 | 0.16w | 0.63w |
| 160 | 0.13w | 0.66w |

Fig. 7

KNEE PROSTHESIS

CROSS-REFERENCE TO RELATED APPLICATIONS

This application is a continuation of application Ser. No. 13/389,950 filed on Mar. 20, 2012, filed as Application No. PCT/EP2010/061572 on Aug. 10, 2010.

TECHNICAL FIELD

The present disclosure generally pertains to knee prosthesis, and particularly to knee prosthesis for use in knee replacement surgery.

BACKGROUND

The differences in the functional outcomes of subjects who have undergone total knee replacement surgeries in comparison to subjects with normal knees, have been linked to different kinematics between normal knees and the artificial knee replacements. Medial pivot knee replacements incorporate a congruent ball and socket configuration on the medial compartment of the joint which replicates the anatomic configuration of the normal knee joint and thereby allows for natural patterns of motion when installed into a subject. However, medial pivot knee replacements do not have any guiding features to control the motion of the joint into a normal gait pattern because they lack cruciate ligament structures that interconnect the medial condyles in natural knee joints.

SUMMARY

The present disclosure pertains to a knee prosthesis joint which approximates the motion of a natural knee, for replacement of a subject's natural knee joint having a width "w" wherein the knee prosthesis has a width "w" and comprises a femoral component having a ball-like condyle on the medial side and a tibial component having a corresponding medial cavity for engaging the medial ball-like condyle. The ball-like condyle, also referred to herein as the "ball", has a center "Mb" and a radius "Rb", while the tibial cavity on the medial side has a spherical bearing surface "Sb". When engaged together, the femoral component and the tibial component of the knee prosthesis define a Cartesian coordinate system X, Y, Z projecting from the tibial component with its origin at "0" which coincides with a center point "Mb" in the medial ball-like condyle. There exists a theoretical trace-line "Lt1" of contact points "Pt1" on the surface of the lateral compartment for the tibial component as a hypothetical predetermined curve on a theoretical spherical surface "Sc1" which has its centre at the origin "0" and a radius in a range of "Rc1"=0.65 w±0.25 win that at a given flexion angle γ for each contact point "Pt1", there exists on a second theoretical trace-line "Lt2" a common contact point "Pt2" on a theoretical sphere "Sc2" projected onto the femoral component. Theoretical sphere "SC2" is identical to "Sc1" and originates from "0" with a radius "Rc2"="Rc1" wherein Rc1 is the radius of the theoretical tibial sphere and Rc2 is the radius of the theoretical femoral sphere, whereby at the given flexion angle γ there exists a plane "E1" through origin and the common theoretical contact point "Pt1/Pt2", which contains the same theoretical guiding curves "Bi" and "Be" on the tibial component and the femoral component. Theoretical guiding curve Bi projects towards medial and theoretical guiding curve Be projects towards lateral. Both theoretical guiding curves Bi and Be stay in a geometrically fixed relation to the common contact point Pt1/Pt2 while their shapes progressively change in opposite directions by changes in flexion angle γ thereby enabling an enforced gliding and rolling movement in both flexion and extension directions.

An advantage of the present knee prosthesis is that there is a clear guidance for pivoting of the tibial component about the medial side of the femoral component as a function of the flexion angle γ as long as there is joint compression applied due to muscle forces, weight, and ligament tensions, to enforce contact between the tibial component and the femoral component. The geometries of the medial and lateral sides are designed to satisfy the kinematic degrees of freedom and the geometric constraints required for proper guiding relative to the characteristics of the expected kinematics. Proper guiding can only be provided by considering certain relationships between the characteristics of the expected kinematics and the geometries of the spherical bearing surfaces of the medial condyles and the guiding surfaces of the lateral condyles. In other words, proper kinematic control is provided by taking into account the expected kinematics patterns (i.e. the exact direction of rolling and sliding of the surfaces) as an input during design of both femoral and tibial components.

The locations of contact on the guiding surfaces do not interfere with the locations of cruciate ligaments or with the location of the patellar groove on the femoral component thus providing options: (i) for preserving the cruciate ligaments, and (ii) for having an anatomical shape for the trochlear groove on the femoral component to enhance the natural articulation of the patella for the full range of motion of the present knee prosthesis from full extension to deep flexion.

Another advantage of the present knee prosthesis is that the complete geometric relationships required to generate the complex 3D geometries of the guiding surfaces are clearly defined. Since the geometric relationships are defined as functions of the width of the knee joint, they can be used to generate any size of the prosthesis when the width is known. If the theoretical guiding curves Bi and Be are arcs with geometries which are defined with mathematical functions, programming of designs for the guiding surfaces becomes easier. These arcs can be parts of the hypothetical circles tangent at the common theoretical contact point Pt1/Pt2 to the line "T2" in plane E1 which is drawn from the common theoretical contact point to the surface "Sb" of the ball.

An embodiment of the present disclosure pertains to generation of a theoretical three-dimensional trace-line Lt1 using a simple generator with data inputs comprising measurements collected from a cadaveric specimen. The generator is defined in a sagittal plane and is projected orthogonally from the sagittal plane to the spherical surface "Sc1" of the tibial component. The generator may be a continuous curve located between two hypothetical circular boundaries with radii R1 and R2 that have a common centre "Ms" with coordinates defined with respect to the aforementioned Cartesian coordinate system wherein (i) x=0.07 w; y=−0.794 w; z=0.5 w, (ii) radius R1=0.54 w+0.08 w, and (iii) radius R2=0.54 w−0.08 w. Because cadaver knee joint dimensions vary among specimens, a middle range for the limiting radii is proposed with R1=0.54 w+0.03 w and R2=0.54 w−0.03 w.

Another embodiment of the present disclosure pertains to clearly defining relative movements between the tibial and femoral components as rotation about a 3D axis passing through the centre of "0". This is achieved in that: (i) at each flexion angle γ, a tangent line T1 to the theoretical trace-line Lt1 at the tibial contact point Pt1, is also the tangent to the theoretical trace-line Lt2 on the spherical surface Sc2 of the femoral component, and (ii) a momentary rotational axis for the movement between the two spheres Sc1/Sc2 is therefore located on a theoretical plane E1, which is perpendicular to the common tangent T1. Therefore, knowing the exact kinematics that should be generated by the surfaces through their interactions, for each flexion angle γ the orientation of the momentary axis of rotation and also the magnitude of incremental rotation about this axis can be calculated. This information can be used to generate a theoretical trace-line of contact points on the femoral component Lt2 that matches a corresponding theoretical trace-line of contact on the tibial component Lt1. For this purpose, starting from the upright position (i.e., full extension) where the location of contact points Pt1 and Pt2 is at the most anterior point of Lt1, the location of contact point Pt2 with respect to the femoral component will be recorded, an increment of flexion angle will be imposed to onto the femoral component about the momentary rotation axis located on the plane E1, and oriented as prescribed by the input kinematics. This will move both of the contact points Pt1 and Pt2 to new matching locations on Lt1 and Lt2. The new location of the contact point on Lt2 with respect to the femoral component will be stored and the motion will continue until the end (i.e., full flexion). Connecting the group of Pt2 points stored for various flexion angles will define the Lt2 curve.

The guiding features of the present knee prosthesis have the advantage of not interfering with: (i) the geometric locations of the patellofemoral articulation, and (ii) the location of the cruciate ligaments and their attachment points, thus offering options for bi-cruciate designs, PCL-retaining designs, and a design with a more normal patellofemoral articulation throughout the full range of motion.

Since a natural knee has a congruent configuration similar to the proposed medial ball-and-socket design, a lateral monocompartmental prosthesis can also be developed based on the present disclosure. Another solution can be a prosthesis with two monocompartmental parts, a ball-like medial compartment and a lateral compartment which incorporates the introduced guiding features.

DESCRIPTION OF THE DRAWINGS

Preferred embodiments of the present disclosure are described below with reference to the drawings, wherein like numerals are used to refer to the same or similar elements:

FIG. 2A shows a cross-sectional vertical cut through the tibial component of the knee prosthesis shown in FIG. 1, along the YZ plane;

FIG. 2B shows a top view of the tibial component shown in FIG. 2A with a trace-line Lt1;

FIG. 2C shows a cross-sectional side view of the tibial component shown in FIG. 2A, with a cut along a trace-line La on a spherical surface Sc1 with a curve Lc in a sagittal plane 4;

FIG. 7 is a table showing the dimensions of the radii for the lateral guiding curves and their corresponding flexion angles γ;

FIG. 8A is a cross-sectional view of the femoral component 3 from FIG. 1 showing an extended position, while

DETAILED DESCRIPTION

Figure 1:
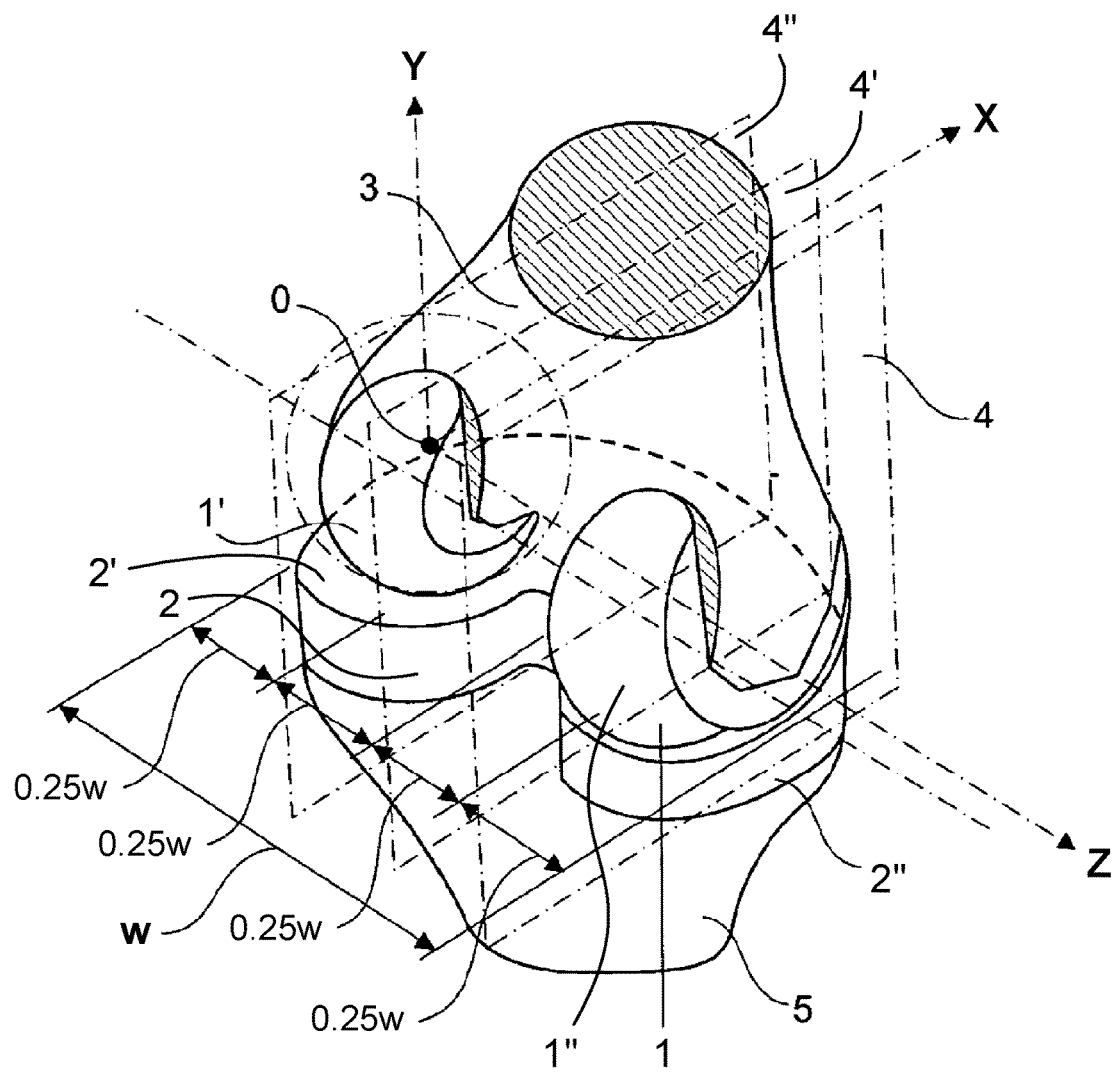
FIG. 1 shows a posterior perspective view of a knee joint prosthesis with a Cartesian coordinate System X; Y; Z.

The present disclosure pertains to a method for constructing a knee prosthesis (FIGS. 1, 2, 8) for a knee joint having a width "w" with a ball-like femoral condyle and a corresponding tibia cavity on the medial side, the ball and the cavity having a centre Mb, a radius Rb, a spherical surface Sb and defining a Cartesian coordinate system X, Y, Z attached to the tibial component of the knee prosthesis with its origin "0" at the centre Mb, comprising:

a first step wherein on the lateral compartment of the prosthesis, a trace-line Lt1 of contact points Pt1 for the tibial component is generated as a predetermined curve on a theoretical spherical surface Sc1, which has its centre at the origin "0" and which has a radius in a range Rc1=0.65 w+/−0.25 w;

whereby at a given flexion angle γ for each contact point Pt1 there exists on a trace-line Lt2 a common contact point Pt2 for a theoretical spherical surface Sc2 attached projecting onto the femoral component of the prosthesis, which is identical to Sc1 and has origin "0" and radius Rc2=Rc1;

a second step of constructing the trace-line Lt2 by incremental steps whereby at each increment of flexion a corresponding magnitude of increment for a pivoting angle β with respect to flexion angle γ is taken from a known relationship β as a function of γ for a further point Pt2 of the trace-line Lt2, which falls together with the new point Pt1 on the predetermined curve, which represents the trace-line Lt1;

a third step of adding the guiding curves Bi and Be for each pair of the corresponding angles γ and β in the corresponding plane E1, whereby at a given flexion angle γ there exists a plane "E1" through origin "0" and the common contact point Pt1/Pt2, which contains the same guiding curves Bi and Be on the tibial component and the femoral component of the knee prosthesis, Bi towards medial and Be towards lateral, both of which stand in a geometrical fixed relation to the common contact point Pt1/Pt2;

and a fourth step of generating guiding curves Bi and Be for the femoral component and the tibial component over the full range of γ and β in a density, which allows machining of the lateral guiding surfaces for the tibial component and the femoral component, for example, by numerical controlled machine tools.

The predetermined curve of the tibial contact points may be generated by interference on the spherical surface Sc1 with a surface of a hypothetical cylinder, which stands orthogonal to a sagittal plane and which is constructed by a continuous curve Lc located on the sagittal plane:

The continuous curve Lc, used to construct the hypothetical cylinder lies on the sagittal plane and between two circular boundaries with radii R1 and R2, which have a common centre Ms with the coordinates X=0.07 w; Y=−0.794 w; Z=0.5 w, radius R1=0.54 w+0.08 w, and radius R2=0.54 w−0.08 w. These dimensions may be restricted to a radius R1 taking R1=0.54 w+0.03 w and radius R2 taking R2=0.54 w−0.03 w.

It is to be understood that, at each flexion angle γ, a tangent T1 to the trace-line Lt1 at the contact point Pt1 is also the tangent for the trace-line Lt2 on the spherical surface Sc2 of the femoral component of the prosthesis and that at each flexion angle, the location of a momentary rotation axis is on a plane E1 which passes through the centre Mb of the medial ball and is perpendicular to the tangent T1 of the three-dimensional trace-line Lt1 at contact point Pt1 for the tibial component of the prosthesis.

The guiding curves Bi and Be may progressively change their shapes in opposite directions by changing flexion angle γ to generate an enforced gliding and rolling movement in both flexion and extension directions. Additionally, conical surfaces can be added for additional support on the interior sides of the trace-lines Lt1 and Lt2, which have their centres at the centre Mb of the medial ball and which have the trace-lines Lt1, Lt2 as generators for the cones.

The guiding curves Be and Bi may be arcs, which start from common contact points Pt1/Pt2. In order to come close to the location of natural guiding surfaces, the guiding curves Be and Bi at the contact points Pt1/Pt2 may be tangent to a line T2 on the plane E1, which is drawn from the common contact point Pt1/Pt2 to the surface Sb on the ball, whereby the plane E1 is orthogonal to a tangent T1 of the trace-line Lt1 at the common contact point Pt1/Pt2.

The guiding curves Be and Bi may be circular arcs with radii Re and Ri, and the curves for the tibial component of the prosthesis may be less congruent to the corresponding guiding curves of the femoral component of the prosthesis in the middle range of flexion angle γ than for the end positions at full extension and at full flexion.

FIG. 1 shows a femur bone 3 and tibia bone 5 with their prosthetic parts in an extension position. The parameter "w" defines the width of the tibial component 2 in the mediolateral direction. The medial and lateral sagittal planes 4 are defined parallel to the sagittal plane of the tibia 5 and passing through the medial and lateral centre of the tibial component 2 at a distance of 0.25 w from the midpoint 6 (FIG. 2A) of the width "w". A Cartesian coordinate system X, Y, Z has its centre "0" on the medial sagittal plane. The X, Y, and Z axes in this coordinates system point to the anterior, proximal, and lateral directions respectively.

FIGS. 2A, 2B, and 2C illustrate the position and the shape of a lateral cavity 8 in the tibial component 2. Starting from the midpoint 6 of the line that connects the medial and the lateral centre of the tibial component, a reference coordinate system is defined having its origin "0" by 0.25 w in medial direction, by 0.32 w in proximal direction and by 0.07 w in posterior direction. From origin "0", the X-axis points towards anterior, the Y-axis points towards proximal and the Z-axis points towards lateral. The centre Mb of the ball-like medial condyle 1 is at the origin "0" and the radius of the medial ball is Rb=0.32 w.

The shapes of the lateral condyles are generated by first defining the trace-lines Lt1, Lt2 of contact points Pt1, Pt2 on the lateral compartment. Two identical spherical surfaces are defined, one surface Sc1 projecting from the tibia and one surface Sc2 projecting from the femur. These spheres are defined concentric with the medial ball when the joint is at full extension and with their radii Rc1 and Rc2 equal to 0.65 w. The trace-lines Lt1 and Lt2 of contact points are both located on the corresponding spherical surfaces Sc1 and Sc2. As can be seen in FIG. 2A at the common contact points Pt1/Pt2 on the lateral side, the shapes of the guiding curves Be, Bi for the tibial and femoral condyles are identical. During the motion of the joint, the two reference spheres Sc1 and Sc2 always remain concentric, causing the spheres to slide on top of each other while tangency between the trace-lines Lt1, Lt2 is maintained.

The three-dimensional trace-line Lt1 of contact points Pt1 is generated by projecting a two-dimensional curve in the lateral sagittal plane 4 on the spherical surface Sc1 of the tibia component in the mediolateral direction. In this example (FIG. 2C), the curve is a circular arc in the lateral sagittal plane 4, having a radius R=0.54 w and its centre Ms is located at x=0.07 w; y=−0.794 w; z=0.5 w defined with respect to the above-mentioned coordinate system. This circular arc lies between two boundaries defined by two arcs with the same centre and with radius of R1=0.54 w+0.08 w and R2=0.54 w−0.08 w as shown in FIG. 2C. The location of a projected contact point Pt1 on the arc Lc is driven from the point Pt1' (FIG. 2B) on the medial sagittal plane location of which is defined by angle α defined between the reference line that passes through the point Pt1' and the centre of the arc and a proximal-distal reference line on the lateral sagittal plane (FIG. 2C). So for each flexion angle, the contact point on the lateral sagittal plane Pt1' and the corresponding Pt1 is defined by the arc and a corresponding angle α. Therefore, the 3D trace of contact points on the tibial component Lt1 is produced by projecting the arc Lc on the spherical surface Sc1. It is to be understood that the arc Lc on the sagittal plane is part of a cylindrical surface, which stands orthogonal to the sagittal plane and which interferes with the spherical surface Sc1.

Figure 3:
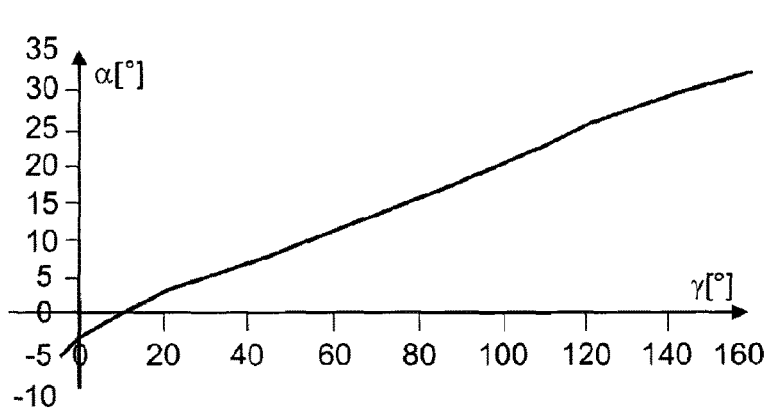
FIG. 3 is a graph showing the angular location of contact points Pt1 in a lateral sagittal plane having angle α as a function of flexion angle γ with some values for the angular relationship shown in the table.

FIG. 3 illustrates in a graph and a table, the values for angle α for flexion angles γ ranging from −5° to 160°. With the flexion angle γ increasing, the lateral contact point Pt1 continuously moves in the posterior direction along the trace-line Lt1 (FIGS. 2B, 2C). When the motion is reversed, the contact point Pt1 will sweep the same exact path in the opposite direction.

The matching trace of contact points on the femoral component is created by keeping the tibial component fixed, and incrementally moving the femoral component with respect to the tibial component starting from −5° of flexion and finishing at 160°, following the input kinematics; in each increment the point Pt1 on the trace-line Lt1 of contact points of the tibial component which is associated with the current flexion angle is added as a contact point Pt2 to the femoral sphere Sc2. The motion continues until 160°, and at the end, all the Pt2 points added to the femoral component form the trace-line Lt2 of femoral contact points. Because of the identical geometries of the tibial component and femoral spheres, the trace of contact points Lt2 on the femoral component is exactly placed over the femoral sphere Sc2.

Figure 5:
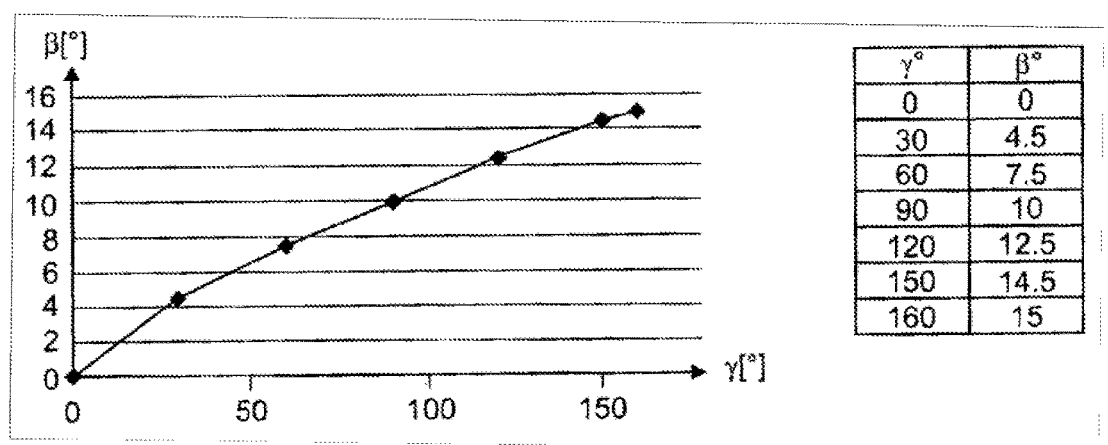
FIG. 5 is a chart showing the pivot angle β of the femur with reference to the tibia as a function of the flexion angle γ, and also some values for the angular relationship in the table.

It is common general knowledge that the flexion axis is on a plane E1 parallel to the XZ plane of the tibia and the pivoting axis is defined perpendicular to the flexion axis on reference plane E1. As shown in FIGS. 3, 5, results collected from testing with cadavers are useful inputs for mathematical modelling of implant surfaces.

Figure 4:
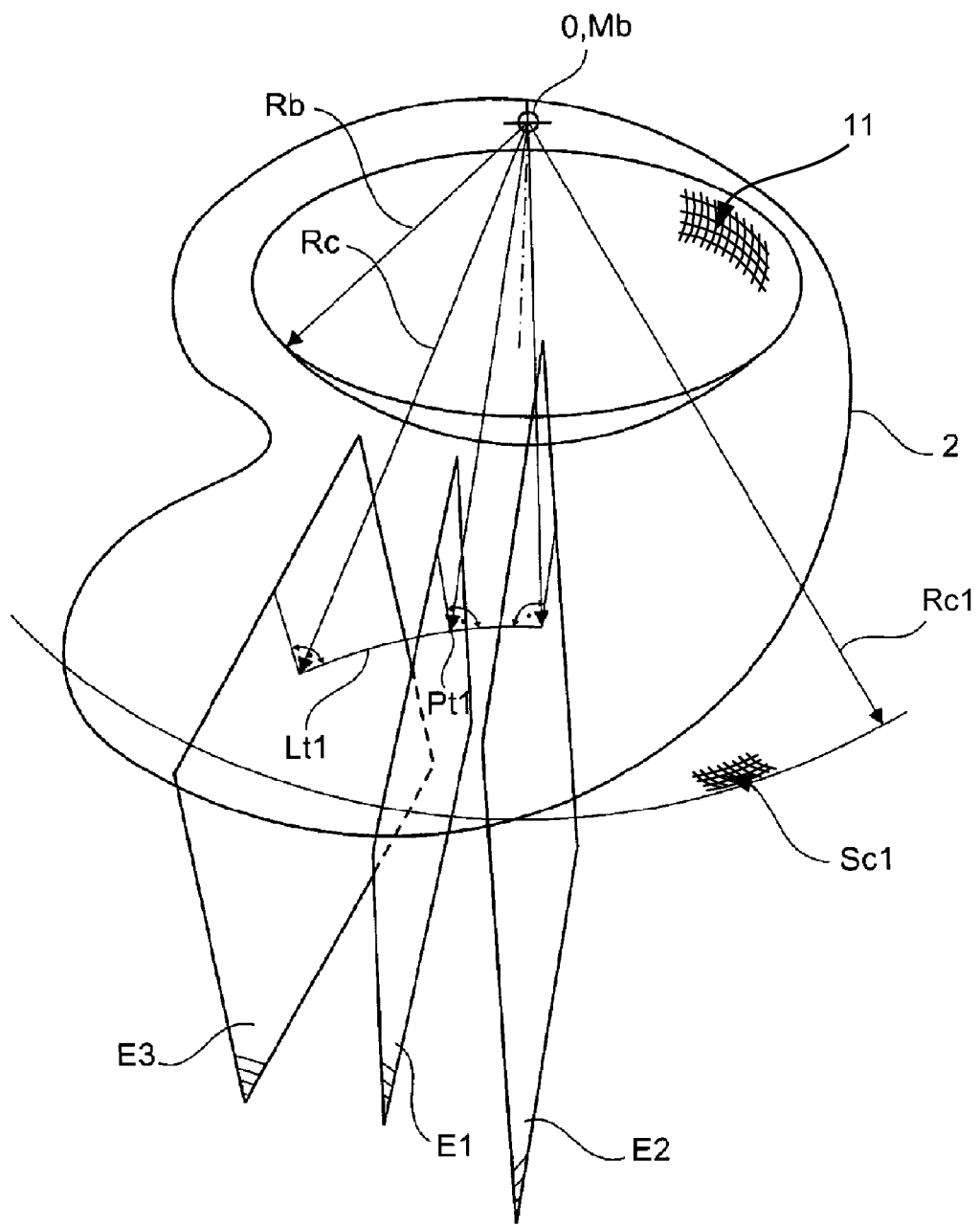
FIG. 4 is a perspective view of a portion of the tibial component 2 shown in FIG. 2 with plane E1, which passes through a centre "0", and a contact point Pt1, perpendicular to the tangent of a trace-line Lt1 at the point Pt1.
Figure 6:
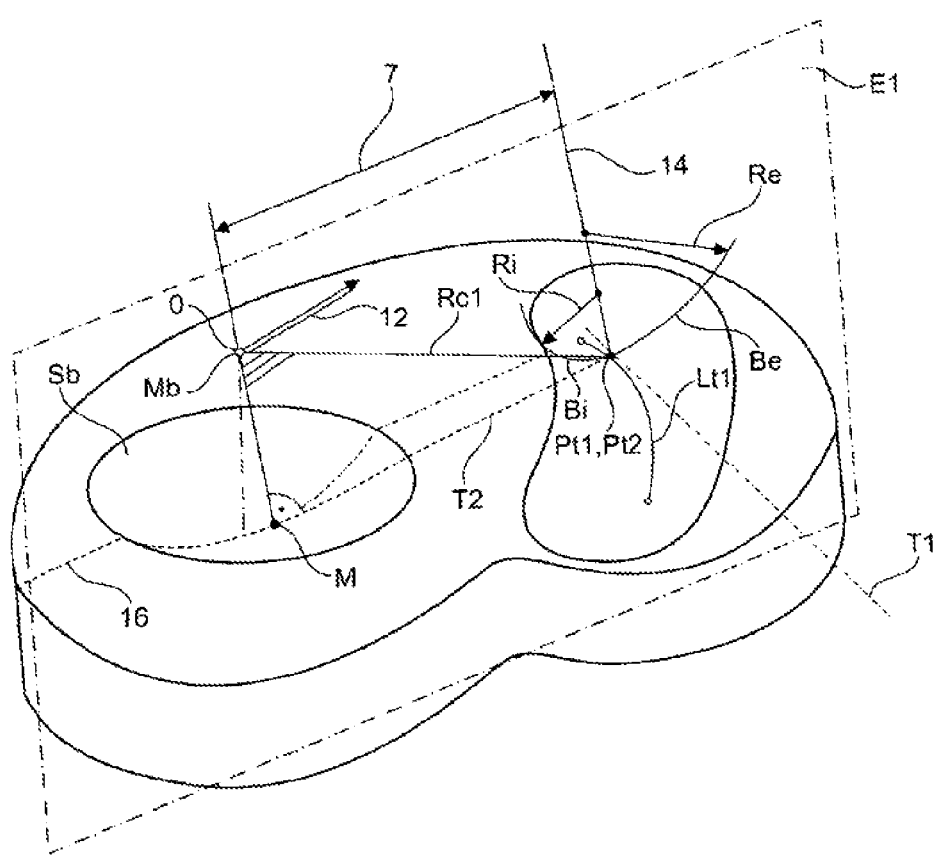
FIG. 6 is a perspective view of the tibial component 2 shown in FIGS. 2B, 2C from the posterior of the tibial component, a plane E1 with the geometrical relationship between the lateral guiding curves Be and Bi and the medial spherical surface Sb.

In reference to FIGS. 4 and 6, at each moment of motion, the locations of contact points on the tibia Pt1 and femoral sphere Pt2, which are associated with the current flexion angle $\gamma$, will be identical (also written as Pt1/Pt2).

The motion from −5° of flexion to 160° flexion for example is broken down into 25 increments (increment of flexion is calculated as 165/25=6.6.degree.).

From one increment to another, the femoral component rotates about the centre of the medial ball.

At each flexion angle, the location of the momentary rotation axis 12 is on the plane E1, which passes through the centre Mb of the medial ball 1 and is perpendicular to the common tangent T1 to the three-dimensional trace-line Lt1 at contact point Pt1 for the tibial component and the trace-line Lt2 at contact point Pt2 for the femoral component. The planes E2 and E3 show the end joint positions, at full extension and full flexion (FIG. 4).

Figure 8A:
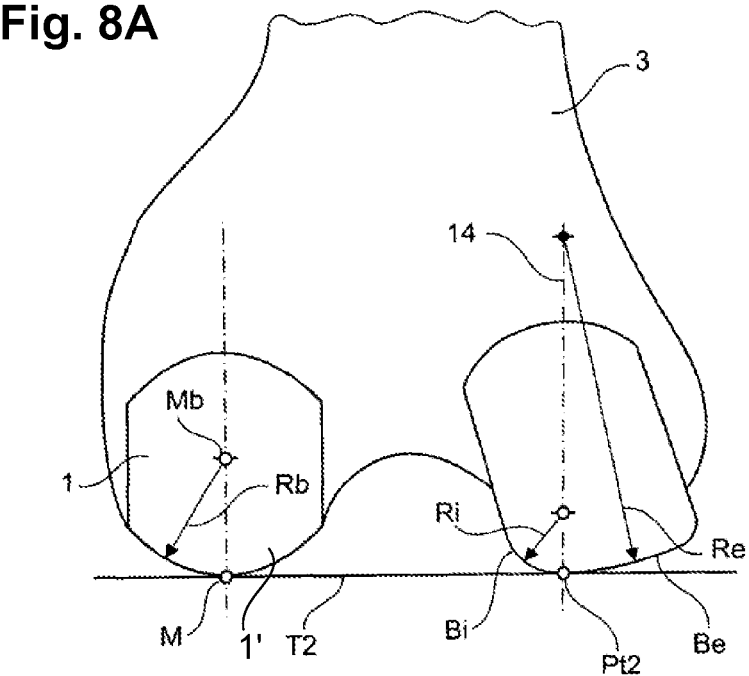
Figure 8B:
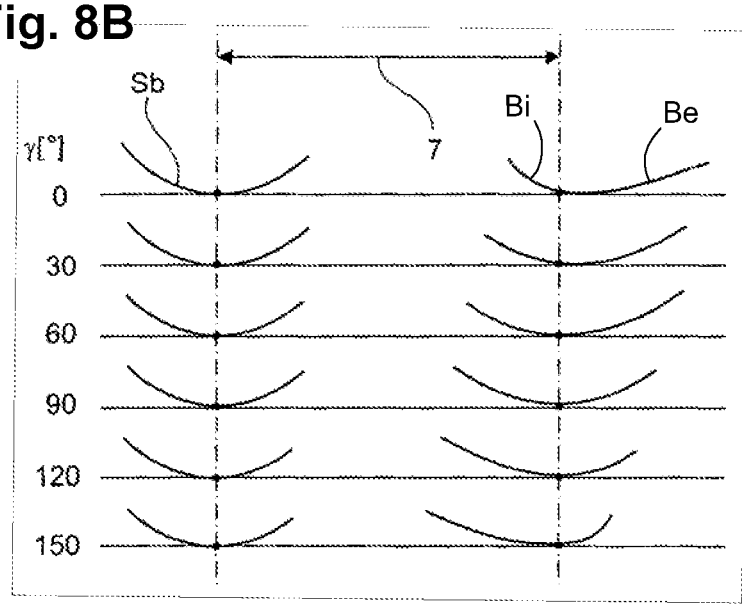
FIG. 8B is a schematic illustration of the changes in the shape of the guiding curves for different flexion angles γ.

The following parameters are to be considered during mathematical modelling of the load-bearing surfaces of the replacement knee prosthesis of the present disclosure:

1. Rotation of the femoral component with respect to the tibial component in each increment is assumed to have two components namely flexion and pivoting.
2. The orientation of the momentary flexion axis is assumed to be on the plane E1, and passes through the centre of the medial ball and is parallel to the XZ plane.
3. The orientation of the pivot is considered to be on the plane E1, and passes through the centre of the medial ball and is parallel to the XY plane.
4. For each increment of motion, the location of the contact point Pt1 is defined as disclosed above. The size of the contact arc can be scaled to accommodate variations in the anteroposterior-to-mediolateral width of knee joints resulting from gender and ethnic differences.
5. The magnitude of incremental flexion is calculated to be 6.6° as described above. The corresponding magnitude of increment for each pivoting angle $\beta$ with respect to the tibial component is extracted from the graph and table shown in FIG. 5. FIG. 5 illustrates how the pivoting of the tibial component takes place as the flexion angles $\gamma$ increases/decreases. It is to be understood that the graphs shown in FIGS. 3 and 5 can be approached by mathematical continuous functions, for example with polynomial equations within the shown limits. It is also to be understood, that these graphs and functions can be slightly varied to obtain different results for the trace-line Lt1 on the tibial component and the trace-line Lt2 one the spherical surface Sc2 of the femoral component.
6. At each increment of motion, the guiding curves Be and Bi on the lateral side of the tibial and femoral components are defined on the plane E1 (FIG. 6). The guiding curves Be and Bi of the tibial and femoral components pass through the momentary common contact points Pt1/Pt2. As mentioned before, plane E1 passes through the centre Mb of the medial ball and stands orthogonal to the trace-line Lt1 at the contact point Pt1 of the tibial component as well as orthogonal to the trace-line Lt2 at the same contact point Pt2 of the femoral component. Two reference lines are constructed on plane E1. The tangential reference line T2 is considered on plane E1 as the line that passes through the point of contact Pt1/Pt2 and is tangent at point M to the medial spherical surface Sb. An orthogonal reference line 14 on plane E1 is considered as a line passing through the contact point Pt1/Pt2 and perpendicular to the tangential reference line T2.
7. In accordance with the described geometric relationships, at each moment of motion there exists a triangle (Pt1/Pt2-O-M) on plane E1 with a shape that always remains unchanged during motion. Because of this, the bearing spacing 7, which is the distance between the medial contact point M and the lateral contact point Pt1/Pt2, will always remain constant during motion (FIG. 2A).
8. As shown in FIG. 6, the plane E1 cuts through the tibial component and the intersecting line at the top surface is shown by a phantom line 16. The shape of the guiding curves Be and Bi on the lateral side for the femoral component and the tibial component is a combination of two circular arcs on both sides of the contact point Pt1/Pt2. These arcs are called interior and exterior arcs, and are labelled according to their radii as Ri and Re, respectively. These arcs are tangent to the line T2 at their starting point Pt1/Pt2 and centres of the arcs lie on the orthogonal reference line 14.
9. The radii Ri and Re of these guiding curves Bi and Be progressively change their shapes in opposite directions with changing flexion angle $\gamma$. This generates an enforced gliding and rolling movement in both directions, as the femoral trace-line Lt2 is much longer than the tibial trace-line Lt1. FIG. 8A shows a posterior view with the definition of the curves Bi and Be. In FIG. 8B the guiding curves Bi and Be for different flexion angles $\gamma$. are drawn on top of each other to make the changes visible. As the spacing 7 between contact point Pt1/Pt2 and point M remains constant, the deepest medial and lateral points are on top of each other, if the reference line T2 is drawn horizontally for the comparison.
10. The dimensions of the radii of the interior and of the exterior guiding curves on the lateral side are defined as functions of the flexion angle $\gamma$ as described in the table shown in FIG. 7. The values are shown dimensionless as decimal fractures of the width w.
11. As shown in the table from FIG. 7, the direction of growth in radius for the interior guiding curve Bi is opposite to that of the exterior guiding curve Be.
12. The guiding curves on the lateral side for the tibial and femoral components on the plane E1 at the common contact points Pt1/Pt2 are constructed based on the same principle. Once a satisfactory shape for trace-lines Lt1 and Lt2 as well as satisfactory shapes for the radii Re and Ri have been found, the guiding curves Be and Bi also have to match the thickness of the tibial component. The increments in the flexion could be chosen to be much smaller to have a sufficient description of the surface for manufacturing. Sometimes it might be helpful to have a rim 13 on the lateral side (FIGS. 2A, 2B, 2C) for enlarging the guiding surfaces Be and Bi.

Figure 9:
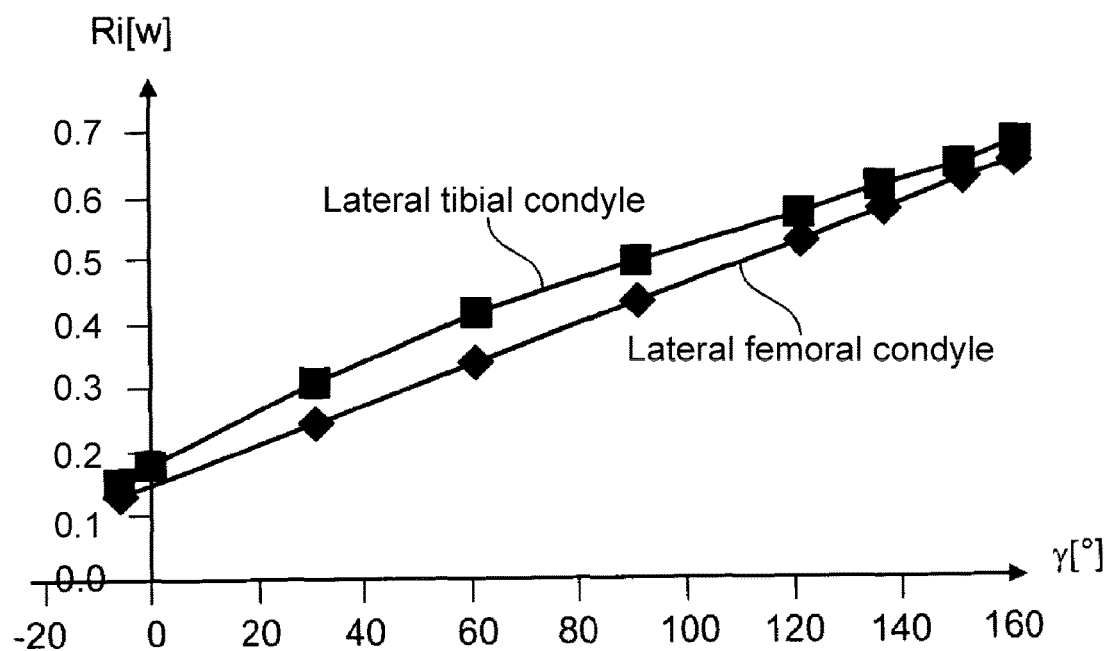
FIG. 9 is a chart showing for the femoral and tibial components, the interior radius Ri as a fraction of the width w depending on the flexion angle γ.
Figure 10:
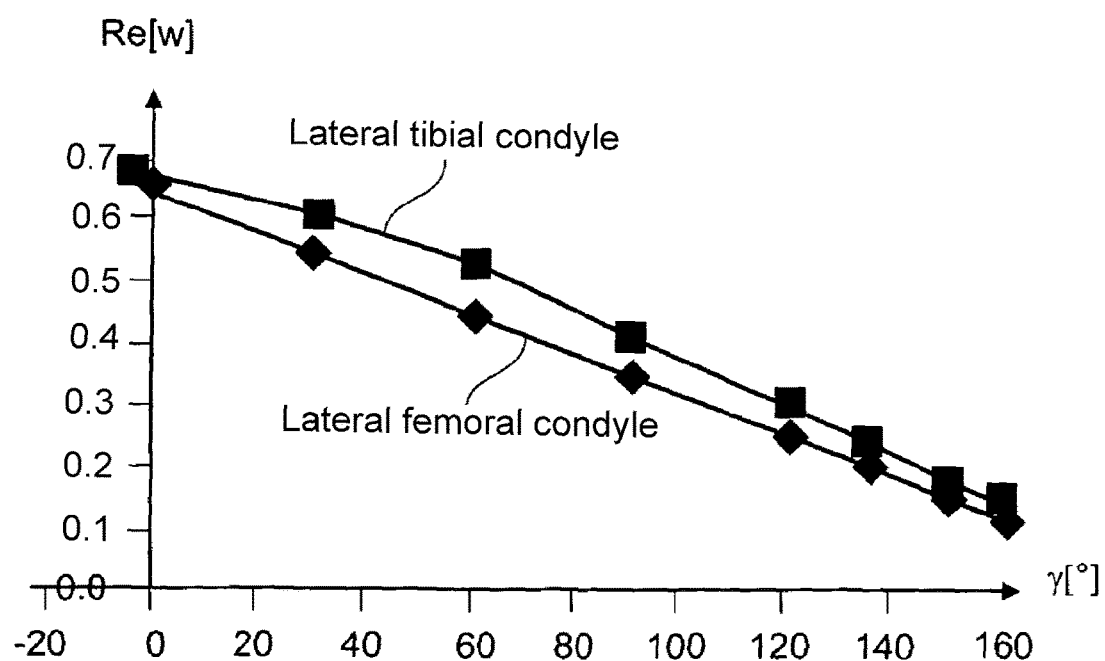
FIG. 10 is a chart showing for the femoral and tibial components, the exterior radius Re as a fraction of the width w depending on the flexion angle γ.

13. As shown in FIGS. 9 and 10, the radii of the guiding curves on the tibial component are considered larger compared to the dimensions of their corresponding guiding curves of the femoral counterpart thereby allowing for clearance and controlled laxity at different flexion angles.

14. The clearance between the tibia and femoral contact curves allows laxities. The magnitudes of these laxities are smaller for the full extension and full flexion positions of the joint. For the mid-range of motion these laxities are larger, due to larger clearances incorporated into the corresponding parts of the contact surfaces.

It is to be noted that trace-lines Lt1 and Lt2 are very important as they are the basis for the definition of the guiding surfaces. They are virtual lines for the definition of the guiding surfaces and for the relative motion between femur and tibia.

Figure 11:
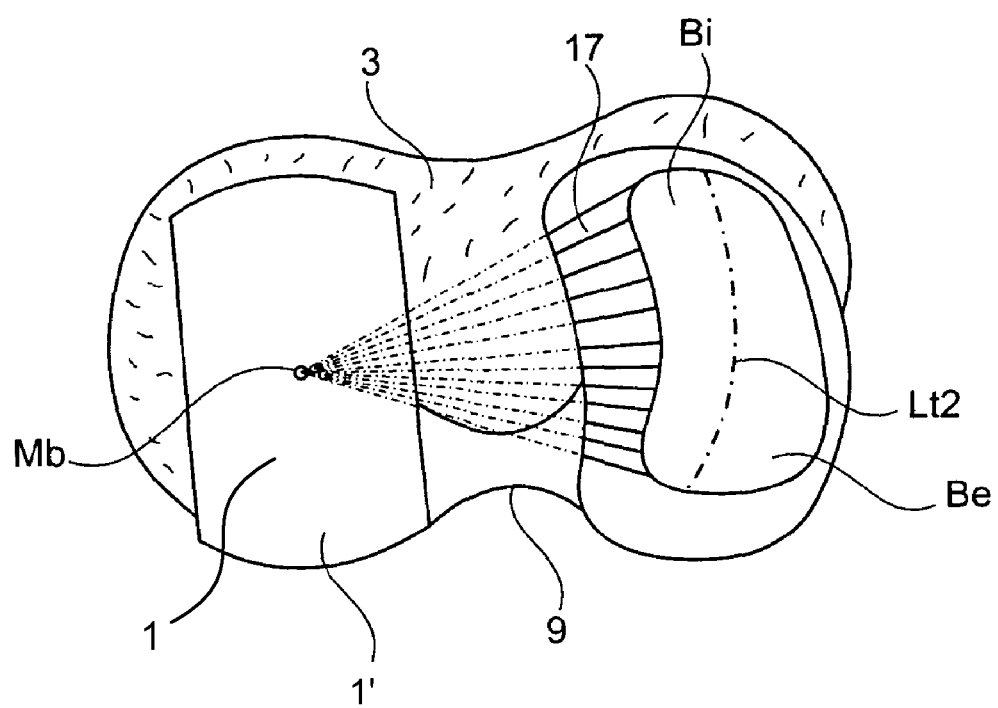
FIG. 11 is a perspective distal view of a femoral prosthesis part having an additional conical surface.
Figure 12:
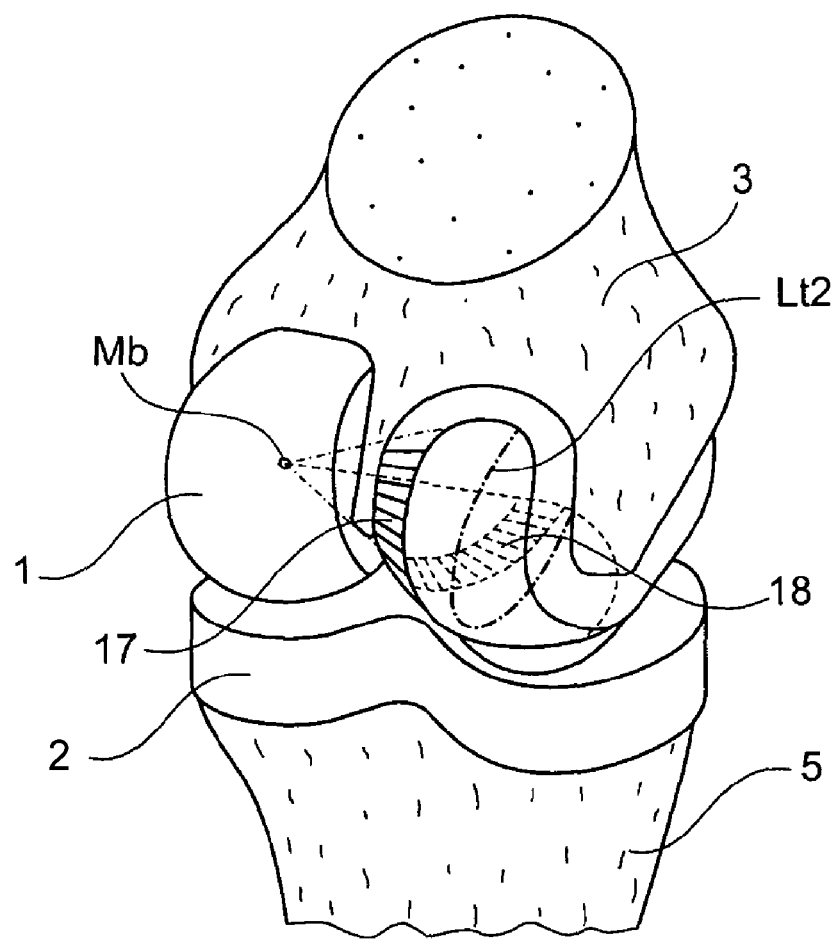
FIG. 12 is a perspective view from a posterior angle of a knee prosthesis with additional conical surfaces.

Trace-lines Lt1 and Lt2 can also be used for defining underlying conical surfaces 17, 18 that control the rolling-gliding of the surfaces. Two cones with their centres at the centre Mb of the medial ball 1 roll and glide over the top of each other. The first cone for the tibial component has the trace-line Lt1 as a generator for the conical surface 18; the second cone for the femoral component has the trace-line Lt2 as a generator for the conical surface 17. There is rolling and gliding possible on these guiding surfaces on the two cones but the rolling and gliding is not particularly enforced by the cones. To some extent the cones can serve as auxiliary supporting surfaces at the lateral interior side of the trace-lines Lt1 and Lt2 in combination with the above described enforced gliding and rolling system. FIG. 11 is a view from approximately distal, which shows a conical surface 17 at the lateral femoral condyle. A band of this conical surface 17 could provide additional articular surface and support to its matching tibial counterpart 18, whereas the relation between gliding and rolling is controlled by the guiding curves Bi and Be. In FIG. 12, the conical surface 18 is shown on the tibial component 2 as if the lateral femoral part was transparent.

Figure 13:
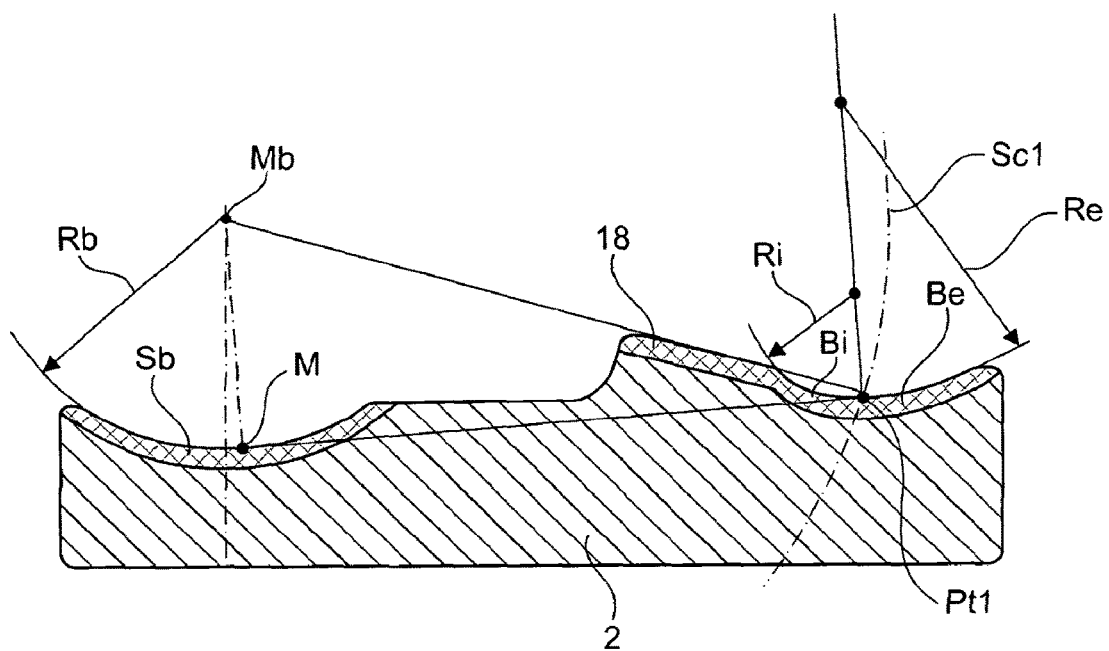
FIG. 13 is a cross-sectional side view of a cut through the tibial part along a plane E1 at full extension with the bearing surfaces.
Figure 14:
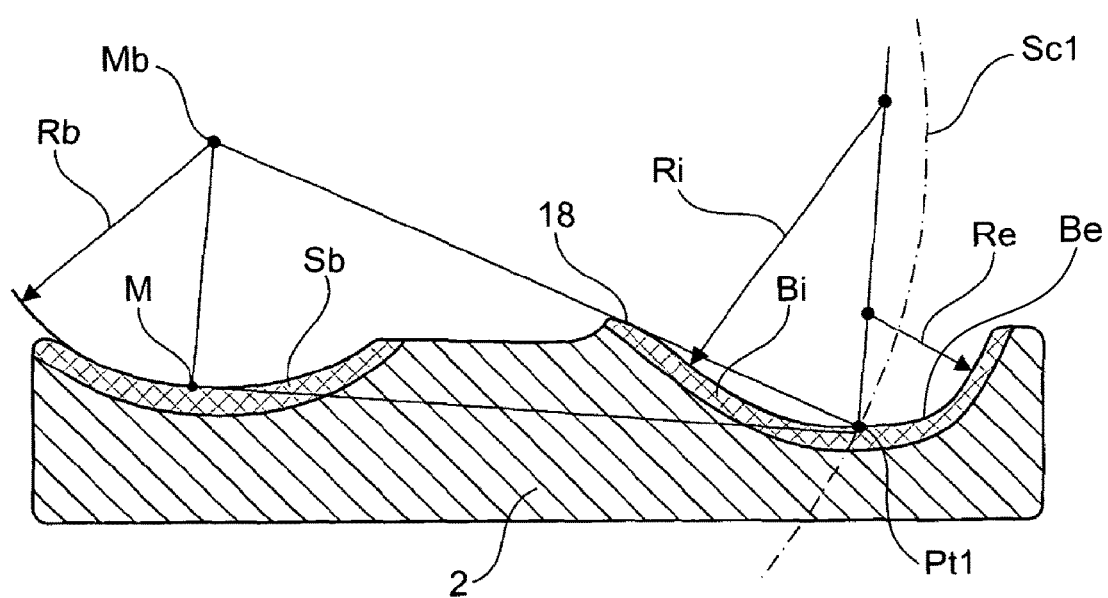
FIG. 14 is a cross-sectional side view of a cut through the tibial part shown in FIG. 13 along a plane E1 for a large flexion angle with the bearing surfaces.

The lateral tibial condyle shown in FIGS. 13 and 14 has a large conical bearing surface 18 in extension and a small conical bearing surface 18 at a large flexion angle γ. This arrangement allows for sufficient bearing surface at all flexion angles.

Depending on a situation when the anterior cruciate ligament (ACL) is present or the posterior cruciate ligament (PCL) is present, these ligaments would be working as secondary mechanisms to guide the rolling and gliding motion. This situation can result in two competing mechanisms that try to override each other in guiding the motion. To solve such a situation, the clearances between the tibial and femoral guiding features can be enlarged by machining the tibial parts with slightly larger guiding curves for the medial and lateral aspects. Having such different tibial parts available would enable a surgeon to choose one that would suit best a patient depending on the condition of their cruciates.

Though a basic lateral guiding surface of the tibia can be defined mathematically, the first guiding surface, which drives the motion from extension to flexion and the second guiding surface, which drives the motion from flexion to extension may not be engaged simultaneously at the same flexion angle. Such guiding surfaces would form an envelope of laxities around a central path, whilst still allowing for steering effects of the contact surfaces. The range of laxities can be set correspondingly for different types of prostheses including ACL or PCL deficient knees.

Practically there are several possibilities to create a wanted laxity at the tibia side.

For example, in reference to FIGS. 9 and 10, the radii Re and Ri could be made larger. The envelope of laxity shifts from anterior to posterior position as the flexion angle increases. The width of an envelope of laxity changes by flexion imposing more laxity for a mid-range of motion and less laxity (more stability) at small and at large flexion angles.

For example, in reference to the example shown in FIG. 6, the guiding curves Be and Bi could be slightly shifted in: (i) the plane E1 for a middle range in the direction of the tangent T2; (ii) the exterior guiding curve Be to spheres with a larger radius Rc, and (iii) interior guiding curve Bi to spheres with a smaller radius Rc. If a third linear segment is added between the two guiding curves, then with an added laxity, the joint might be riding on the third segment without engaging the two guiding curves.

If the material selected for producing the knee prosthesis disclosed herein has enough elasticity, then the trace-line Lt1 or the third segment can deflect thereby allowing for the side curves to partially engage and produce traction. If the material is not sufficiently elastic, then there could be a pinching load between the articular surfaces that could cause surface damage to the tibial component over extended periods. Suitable elastic materials are exemplified by polyurethane (PU), elastomeric PU, polycarbonate urethane (PCU), polyethylene (PE), and ultra-high molecular weight (UHMW) polyethylene.

The invention claimed is:

1. A knee prosthesis for a knee joint having a width (w), said knee prosthesis also having the width (w) and comprising a replacement femoral component (3) defining a medial ball-like condyle and a replacement tibial component (2) defining a cavity on a medial side corresponding to the medial ball-like condyle, said replacement femoral component (3) and replacement tibial component (2) defining a lateral compartment of the knee prosthesis, wherein:

(i) the medial ball-like condyle (1) of the replacement femoral component (3) and the cavity (11) of the replacement tibial component (2) have a centre (Mb), a radius (Rb), a spherical surface (Sb), and define a Cartesian coordinate system X, Y, Z projecting from the replacement tibial component, said Cartesian coordinate system having its origin (0) at the centre (Mb);

(ii) wherein the femoral component follows an articulate path within the lateral compartment defined by a trace-line (Lt1) of a series of distal-most contact points (Pt1) for the replacement tibial component (2) as a predetermined curve (15) on a first spherical surface (Sc1), said first spherical surface (Sc1) having its centre at the origin (0) and a radius (Rc1) in a range of (Rc1)=0.65 w+/−0.25 w, wherein (w) is the width of the knee prosthesis;

(iii) at a given flexion angle γ for each contact point (Pt1) on the replacement tibial component (2), there exists a trace-line (Lt2) of a series of common distal-most contact points (Pt2) for a second spherical surface (Sc2) on the replacement femoral component (3), said second spherical surface (Sc2) identical to said first spherical surface (Sc1), said second spherical surface (Sc2) having its origin at origin (0) and a radius (Rc2=Rc1) whereby at a given flexion angle γ there exists a plane (E1) through origin (0) and a common contact point (Pt1/Pt2) with a guiding curve (Bi, Be) on the replacement tibial component (2) and a complementary guiding curve on the replacement femoral component (3), wherein both guiding curves (Bi, Be) are in a geometrically fixed relation to the common contact point (Pt1/Pt2) for the given flexion angle γ; and (iv) a shape of guiding curves (Bi) and (Be) is progressively changed by each change of flexion angle γ to generate an enforced gliding movement and an enforced rolling movement in a flexion direction and in an extension direction.

2. The knee prosthesis of claim 1, wherein the guiding curves (Bi) and (Be) are arcs with radii (Ri), (Re) projecting from the common contact point (Pt1/Pt2).

3. The knee prosthesis of claim 1, wherein the plane (E1) is orthogonal to a tangent (T1) of the trace-line (Lt1) at the common contact point (Pt1/Pt2) and the guiding curves (Bi) and (Be) at the common contact point (Pt1/Pt2) are tangent to a line (T1) on plane (E1) projecting from the common contact point (Pt1/Pt2) to the surface (Sb) of the medial ball-like condyle (1) of the replacement femoral component (3).

4. The knee prosthesis of claim 1, wherein the predetermined curve (15) is generated by an interference of the first spherical surface (Sc1) with a surface of a hypothetical cylinder, said hypothetical cylinder surface standing orthogonal to a sagittal plane (4) and constructed by a continuous curve (Lc) located on the sagittal plane (4).

5. The knee prosthesis of claim 1, wherein the continuous curve (Lc) used to construct the hypothetical cylinder surface, lies on the sagittal plane (4) between two circular boundaries having radii (R1) and (R2) with a common centre (Ms) with the x, y, z coordinates of x=0.07 w, y=−0.794 w, z=0.5 w, wherein a maximum radius (R1)=0.54 w+0.08 w and a maximum radius (R2)=0.54 w−0.08 w, wherein (w) is the width of the knee prosthesis.

6. The knee prosthesis of claim 5, wherein a minimum radius (R1)=0.54 w+0.03 w and a minimum radius (R2)=0.54 w−0.03 w, wherein (w) is the width of the knee prosthesis.

7. The knee prosthesis of claim 1, wherein at each flexion angle γ, a tangent (T1) to the trace-line (Lt1) at the contact point (Pt1) on the replacement tibial component (2) is also the tangent for the trace line (Lt2) on the second spherical surface (Sc2) of the replacement femoral component (3), and at each flexion angle, the location of the momentary rotation axis (12) is on a plane (E1) which passes through the centre (Mb) of the medial ball-like condyle (1) on the replacement femoral component said momentary rotation axis (12) perpendicular to the tangent (T1) of the three dimensional trace-line (Lt1) at contact points (Pt1) on the replacement tibial component (2).

8. The knee prosthesis of claim 1, built as a total knee prosthesis with (i) a replacement femoral component (3) having a groove (9) similar to a patellar groove, and (ii) the replacement tibial component (2) having a posterior cut out (10) for engaging one or both of a subject's cruciate ligaments.

9. The knee prosthesis of claim 1, wherein the guiding surfaces (Bi) and (Be) for the replacement tibial component and for the replacement femoral component are less congruent for a middle range of the flexion angle γ than for the end positions of full extension and full flexion.

10. The knee prosthesis of claim 1, wherein conical surfaces (17), (18) are added on an interior side of the trace-lines (Lt1) and (Lt2) for additional support, said conical surfaces (17), (18) having (i) their centres at the centre (Mb) of the medial ball-like condyle (1) of the replacement femoral component and (ii) having trace-lines (Lt1), (Lt2) as generators for the conical surfaces (17), (18).

* * * * *